(12) United States Patent
Löning et al.

(10) Patent No.: US 7,959,713 B2
(45) Date of Patent: Jun. 14, 2011

(54) COOLING AND PURIFICATION OF GAS STREAMS

(75) Inventors: Jan-Martin Löning, Freinsheim (DE); Manfred Heckmann, Kuantan (MY); Karl Hölemann, Mannheim (DE); Thomas Heitz, Dannstadt-Schauernheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 899 days.

(21) Appl. No.: 10/593,333

(22) PCT Filed: Mar. 17, 2005

(86) PCT No.: PCT/EP2005/002847
§ 371 (c)(1),
(2), (4) Date: Sep. 19, 2006

(87) PCT Pub. No.: WO2005/089905
PCT Pub. Date: Sep. 29, 2005

(65) Prior Publication Data
US 2008/0236391 A1    Oct. 2, 2008

(30) Foreign Application Priority Data
Mar. 19, 2004  (DE) .................. 10 2004 013 967

(51) Int. Cl.
*B01D 47/00*    (2006.01)
(52) U.S. Cl. ............. 95/237; 95/149; 95/199; 95/223; 95/228; 560/78
(58) Field of Classification Search ............ 95/149–240; 560/78
See application file for complete search history.

(56) References Cited

U.S. PATENT DOCUMENTS

| 3,227,743 | A | 1/1966 | Shaw et al. |
| 3,839,414 | A | 10/1974 | Windle, III |
| 5,434,239 | A | 7/1995 | Bhatia |
| 6,312,503 | B1* | 11/2001 | Fike et al. ............... 95/211 |
| 2003/0114062 | A1* | 6/2003 | Scott et al. ............... 442/181 |
| 2004/0044172 | A1* | 3/2004 | Kulkarni et al. ........... 528/280 |

FOREIGN PATENT DOCUMENTS

| CZ | 134835 | | 7/1969 |
| DE | 160829 | * | 5/1980 |
| DE | 145 540 | | 12/1980 |
| DE | 145540 | * | 12/1980 |
| DE | 160 829 | | 4/1984 |
| DE | 103 16 466 | | 10/2004 |
| EP | 0 741 124 | | 12/1999 |

OTHER PUBLICATIONS

Ullmann's Encyclopedia of Industrial Chemistry, 6th edition, 2000 Electronic Release, Wiley-VCH, Weinheim 2000, p. 237.

* cited by examiner

*Primary Examiner* — Duane Smith
*Assistant Examiner* — Thomas McKenzie
(74) *Attorney, Agent, or Firm* — Connolly Bove Lodge & Hutz LLP

(57) ABSTRACT

Process for purifying and cooling a gas stream comprising a dialkyl ester A) of an aromatic dicarboxylic acid, which comprises treating the gas stream with an aliphatic dihydroxy compound B) at a temperature less than/equal to the melting point of the dialkyl ester A) in a 1st stage and treating the gas stream with an aliphatic dihydroxy compound B) at above the melting point of the dihydroxy compound B) in at least one 2nd stage.

19 Claims, 1 Drawing Sheet

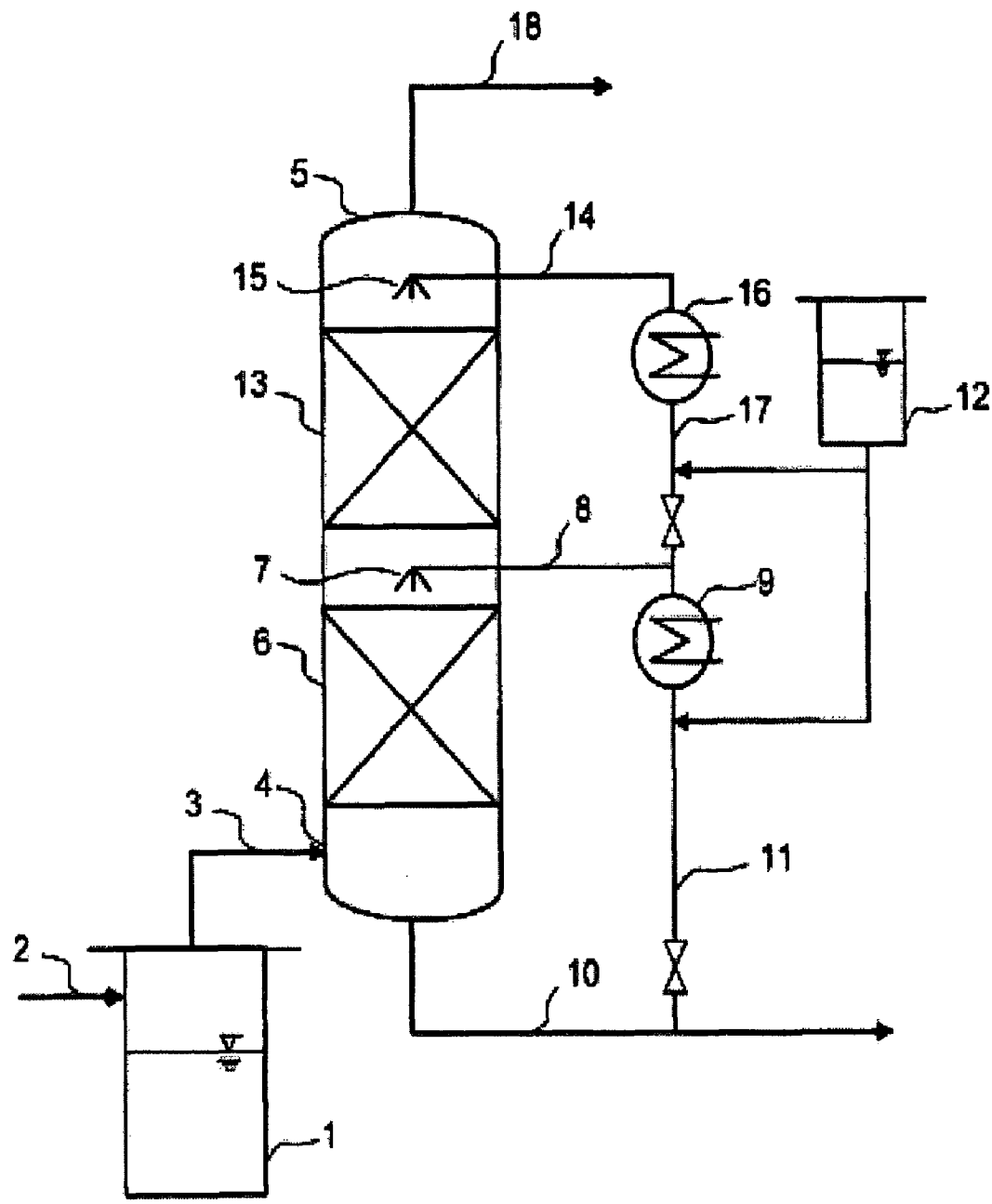

COOLING AND PURIFICATION OF GAS STREAMS

This application is the National Stage of International Application No. PCT/EP2005/002847 filed on Mar. 17, 2005; and this application claims priority of Application No. 102004013967.9 filed in Germany on Mar. 19, 2004 under 35 U.S.C. §119; the entire contents of all are hereby incorporated by reference.

The present invention relates to an improved process for purifying and cooling a gas stream comprising a dialkyl ester A) of an aromatic carboxylic acid.

Aromatic dialkyl esters are industrially important starting materials, for example for the preparation of polyesters of all types.

Dimethyl terephthalate (DMT), in particular, is an important intermediate for the production of various, industrially important polyesters such as polyethylene terephthalate (PET) and polybutylene terephthalate (PBT). For this purpose, DMT is reacted in molten form with the corresponding alcohols ethylene glycol and 1,4-butanediol in the presence of a catalyst and the monomeric intermediates obtained in this way are subsequently converted into the polyesters by polycondensation (Ullmann's Encyclopedia of Industrial Chemistry, $6^{th}$ edition, 2000 Electronic Release, Wiley-VCH, Weinheim 2000).

These dialkyl esters hydrolyze very quickly on contact with water to form (in an equilibrium reaction) the corresponding acid which has an adverse effect on the product quality of the polyester. DMT is generally stored in molten form at 165° C.-170° C. in an inert atmosphere (nitrogen) so that oxidation or hydrolysis of the DMT is prevented and metering into the transesterification is made easier. Hot gas streams laden with DMT are therefore conveyed from the storage tank when further nitrogen is continuously fed in.

In the further polycondensation process, such gas streams are also formed as offgas streams from the polycondensation reactors and esterification stages and also precondensation stages.

On cooling, DMT tends to desublime from the gas phase. This can lead to formation of solid DMT particles which make purification and cooling of DMT-laden gas streams considerably more difficult. If the solid DMT particles are not separated off, the permissible emission limits for DMT can be exceeded.

Various methods of separating off DMT from gas streams by contact with a liquid are described in the literature.

DD-A 160829 describes the scrubbing of DMT-containing gas streams from a PBT reactor with 1,4-butanediol. Here, DMT is stripped out by means of the low-boiling reaction by-product methanol which is separated off by distillation. DMT is separated off from the methanol carrier gas stream in an absorption column using 1,4-butanediol as entrainer at an inflow temperature of 100-150° C. and is recirculated to the reaction zone. Simultaneous gas cooling is not described.

The removal of DMT vapor and DMT particles from a storage tank containing molten DMT by means of water in a cocurrent apparatus is described in U.S. Pat. No. 5,749,944. In an apparatus containing no internals, DMT is separated out by spraying in water at 10-32° C. and the carrier gas stream is simultaneously cooled. An advantage is said to be the fact that low-boiling organic solvents (e.g. methanol) are not used, so that no additional emissions of the scrubbing liquid via the pure gas stream occur. A disadvantage is found to be that a mist-like gas/liquid mixture containing solid DMT particles is emitted due to the strong cooling at the outlet of the apparatus, so that a further unit for precipitating the DMT particles becomes necessary. Due to the contact with water, there is no opportunity of recirculating DMT to the synthesis process. The wastewater stream has to be disposed of. In addition, a special protection device to prevent water flowing back via the crude gas line into the DMT storage tank is necessary.

DD-A 145540 claims the separation and recovery of DMT in PET production using a DMT sublimate separator provided with a glycol seal. The DMT-laden gas streams come from the intermediate storage or melting of DMT. In the sublimate separator, the DMT-containing gas together with fresh glycol are fed in cocurrent at 70-120° C. into the middle chamber of 3 chambers and pushed out by an overpressure of inert gas via a glycol seal (20-160° C.) into an exit chamber for the gas. The DMT dissolved in the glycol can thus be returned to the PET synthesis. Additional gas cooling is not mentioned in this process.

A disadvantage is found to be the entrainment of DMT/glycol solutions which usually require a downstream precipitation vessel.

The scrubbing of DMT-laden gas streams from the DMT synthesis with methanol in a countercurrent apparatus is described in CS 134835. The DMT can be returned to the process after a solid/liquid separation. The volatility of methanol makes it necessary to have a second separation apparatus in which the methanol is separated off from the pure gas stream by scrubbing the gas with water. The temperatures which prevail are not described in more detail. Scrubbing of DMT with methanol is likewise claimed in EP-A 0741124.

DMT can also be recovered from gas streams using xylene (DE-A 2105017) and liquid DMT (U.S. Pat. No. 3,227,743).

A process for the simultaneous purification and cooling of gas streams from the synthesis of PET using ethylene glycol in a two-stage countercurrent scrub is described in U.S. Pat. No. 6,312,503. The hot gas stream (175° C.) from a polymerization reactor for producing PET comprises by-products which are not specified in more detail and also unreacted starting materials, in particular ethylene glycol, acetaldehyde and water.

A two-stage scrub in which the gas is cooled by direct contact with a liquid in the lower section of the apparatus at cooling rates of less than 5.4° C./ft$^2$ (based on the surface area of the internals) is claimed for this purpose. In the upper part of the apparatus, the foreign substances are scrubbed from the inert gas stream by the same liquid at lower temperatures.

Disadvantages of this process are that it merely cools the gas stream and mist formation occurs in the apparatus due to the very high cooling rate and because the lower segment is used for quenching ($\hat{=}$cooling).

DE-A 103 164 66.9 proposes a two-stage procedure in which the 1st stage is carried out at above the melting point of the dialkyl ester.

It is an object of the present invention to provide an improved process for purifying and cooling a gas stream comprising a dialkyl ester A) of an aromatic dicarboxylic acid, which comprises treating the gas stream with an aliphatic dihydroxy compound B) at a temperature less than/equal to the melting point of the dialkyl ester A) in a 1st stage and treating the gas stream with an aliphatic dihydroxy compound B) at above the melting point of the dihydroxy compound B) in at least one 2nd stage.

Preferred embodiments are disclosed in the subordinate claims.

Surprisingly, the process of the present invention leads to a better balance in terms of environmental considerations and capital costs.

Furthermore, the loss of aromatic dialkyl ester used minimized, the energy requirement for the lower scrubbing stage is minimized and at the same time the amount of scrubbing medium carried via the gas phase from the lower scrubbing stage to the upper scrubbing stage is reduced, the gas stream is purified very efficiently (ester content as low as possible), the starting ester is returned to the synthesis, i.e. the space-time yield is increased, desublimation in the apparatus is prevented and the carrier gas stream is at the same time cooled without mist formation, the diols additionally have a high solvent capacity for the esters, so that no precipitation of solid occurs and circulation of the solvent is made possible.

For the purposes of the present invention, the dialkyl esters A) are compounds which are made up of an aromatic dicarboxylic acid with aliphatic ester radicals.

Preferred dicarboxylic acids are 2,6-naphthalenedicarboxylic acid, terephthalic acid and isophthalic acid or mixtures thereof. Up to 30 mol %, preferably no more than 10 mol %, of the aromatic dicarboxylic acids can be replaced by aliphatic or cycloaliphatic dicarboxylic acids such as adipic acid, azelaic acid, sebacic acid, dodecanedioic acids and cyclohexanedicarboxylic acids.

Preference is given to mixtures of from 5 to 100 mol % of isophthalic acid and from 0 to 95 mol % of terephthalic acid, in particular mixtures of about 80% of terephthalic acid with 20% of isophthalic acid up to approximately equimolar mixtures of these two acids.

A very particularly preferred dicarboxylic acid is terephthalic acid.

Preferred alkyl radicals have from 1 to 4 carbon atoms, in particular 1 or 2 carbon atoms. Preferred dialkyl esters are those derived from 2,6-naphthalenedicarboxylic acid, terephthalic acid or isophthalic acid or mixtures thereof, with dimethyl esters being preferred.

Particular preference is given to dimethyl terephthalate (DMT).

As aliphatic dihydroxy compound B), preference is given to using diols having from 2 to 6 carbon atoms, in particular 1,2-ethanediol, 1,3-propanediol, 1,2-butanediol, 1,6-hexanediol, 1,4-hexanediol, 1,4-butanediol, 1,4-cyclohexanediol, 1,4-cyclohexanedimethylanol and neopentyl glycol or mixtures thereof, with 1,4-butanediol being particularly preferred.

The process of the present invention is described in more detail below using the purification and cooling of a DMT-containing gas stream as an example. However, it should be emphasized that the process can be used for purifying and cooling gas streams comprising other dialkyl esters of aromatic dicarboxylic acids.

During storage in a tank, DMT is generally kept in the molten state at from 140 to 286° C., preferably from 165 to 170° C., and blanketed with a dry gas stream, preferably an inert gas stream, in particular a stream of nitrogen.

Preferably continuous displacement of the inert gas stream (due to filling of the tank) results in a DMT-laden gas stream. Such a gas stream is also formed as an offgas stream after the precondensation or after-condensation of polyesters, and this can be purified and cooled in a corresponding fashion by means of the process of the present invention.

For this purpose, the DMT-containing gas stream is treated with the abovementioned dihydroxy compound B) at temperatures less than/equal to the melting point of the dialkyl ester A) in a first stage.

In the case of DMT, the melting point is 140° C., and the temperatures of the gas stream are generally from 140 to 286° C., preferably from 150 to 170° C.

Suitable apparatuses are in general ones which can bring the gas stream into contact with the dihydroxy compound B) either in cocurrent or countercurrent. These are, in particular, trickle film apparatuses, columns containing random packing or ordered packing, apparatuses containing a dispersed liquid phase and a continuous gas phase/spray apparatuses, apparatuses containing gas and a continuous liquid phase, e.g. bubble columns, or tray columns.

To increase the contact area between the phases, the appropriate apparatus is equipped with internals such as trays, random packing, structured packing and other separation-active column internals corresponding to the prior art. The apparatus can also be free of internals and have spraying of the liquid. The component B) is introduced into the gas stream via conventional dispersion devices or nozzles.

The volume flow of gas in storage in a tank is usually from 5 to 75 m$^3$/h, preferably from 25 to 50 m$^3$/h.

The proportion of DMT in the gas stream is limited by the respective saturation vapor pressure in the respective inert gas stream. In the case of $N_2$, this is a maximum of 23% by weight, and effective purification is possible down to a concentration of 0.0001 ppm by weight of DMT in the $N_2$ stream. The concentration of DMT in the $N_2$ stream is usually from 0.001 to 16 ppm by weight.

Based on the abovementioned temperature-dependent saturation vapor pressure in the respective inert gas stream, e.g. 23% by weight in $N_2$, it is advantageous to carry out the process of the present invention as a degree of saturation [%] of the gas stream of less than/equal to 50%, preferably less than/equal to 40%.

The degree of saturation of the gas stream is a measure of the concentration of DMT in the gas phase and is defined by $$\text{Degree of saturation } [\%] = \frac{\text{Partial pressure of } DMT}{\text{Saturation vapor pressure of } DMT} \cdot 100\%$$

$$\triangleq \text{Measure of the concentration of}$$

$$DMT \text{ in the gas phase}$$

(cf. Baehr, H. D., "Thermodynamik", 8th Edition, Berlin, etc., Springer 1992; p. 212 ff).

In the process of the present invention, component B) is added simultaneously or subsequently, e.g. via distributor devices, e.g. nozzles, or in the case of countercurrent operation, preferably at the end of the 1st stage.

The lower limit to the temperature in the 1st stage of component B) is imposed by the melting point of the component A). In the case of a process using DMT as ester, this means less than/equal to 140° C., preferably 140-50° C., and in particular 136-60° C., and very particularly preferably 124-110° C.

The upper limit to the temperature is imposed by the boiling point of the diol used in the particular case. In the case of 1,4-butanediol, the temperature of the purification stage is preferably below 237° C., preferably below 227° C. When ethylene glycol is used as scrubbing medium, the temperature is below 198° C., preferably below 190° C., while in the case of propanediol temperatures below 213° C., preferably below 200° C., are advisable.

To carry out the process, it is possible to use, for example, pure 1,4-butanediol or 1,4-butanediol laden with DMT. The 1,4-butanediol can be brought into contact with the gas either in a single pass or with recirculation. Gas and liquid phase can be introduced at any point in the apparatus corresponding to the above-described principle. The process principle can at the same time be extended to 3-stage and multistage operation.

The pressure in the 1st stage is generally from 1 013 mbar (ambient pressure, atmospheric pressure) to 1 113 mbar, preferably from 1 013 to 1 083 mbar (for storage in a tank).

According to the present invention, DMT is transferred from the gas phase into the liquid scrubbing medium (dihydroxy compound) by the treatment in the 1st stage.

When leaving the 1st stage, the gas stream contains from 0.01 to 1 000 ppm by weight of DMT, preferably from 1 to 50 ppm by weight of DMT.

On leaving the 1st stage, the liquid stream of the dihydroxy compound contains from 0.01 ppm by weight to 59% by weight of DMT, preferably from 0.1 ppm by weight to 10% by weight of DMT.

In the 2nd stage of the process of the present invention, the gas stream is cooled by means of an aliphatic dihydroxy compound B), with it being essential that this stage is carried out at above the melting point of the component B). The temperature in the case of 1,4-butanediol is greater than 19° C., preferably from 20 to 80° C. and in particular from 50 to 70° C., while in the case of ethylene glycol and propanediol the melting points are −10° C. and −32° C., respectively, so that operation in the abovementioned temperature ranges is likewise recommended.

The apparatuses suitable for this purpose and their internals correspond to those described for stage 1.

This also applies to the pressure.

The temperature parameters in the process of the present invention are designed so that the actual DMT partial pressure (content in the gas phase) does not exceed the vapor pressure of incipient desublimation.

On leaving the second zone (which can also be divided into a plurality of zones), the gas stream has a DMT content of from 0.001 to 16 ppm by weight, preferably from 0.01 to 1 ppm by weight.

A particularly preferred embodiment (cf. figure) of the process of the present invention is described in more detail below:

DMT is kept in a molten state in a storage tank (1) and is blanketed with dry inert gas (2) (e.g. nitrogen) to avoid oxidation and contact with water. As a result of continuous displacement of the inert gas (e.g. on filling of the tank), a DMT-laden gas stream (3) is conveyed via a heated gas line and a heated gas inlet (4) to an absorption column (5). In the lower section (6) of the column which is provided with separation-active internals, liquid 1,4-butanediol is conveyed via a distributor device (7) in countercurrent to the gas stream at a temperature of 50° C.<T<139° C. (depending on the degree of saturation). In this way, the DMT is transferred from the gas phase into the liquid scrubbing medium. The liquid stream (8) is preheated to the admission temperature by means of a heat exchanger (9). The stream can either be taken from the bottoms from the column (10) as substream (11) with addition of pure 1,4-butanediol (12) or be fed in as pure 1,4-butanediol (12).

The gas stream which has been depleted in DMT is passed to a second column section (13) which is provided with separation-active internals and is cooled there by direct contact with a second scrubbing medium stream (14) at a temperature of 20° C.<T<140° C. The scrubbing medium stream is introduced into the column via a distributor device (15) and heated by means of a heat exchanger (16). As scrubbing medium stream, it is possible to use pure 1,4-butanediol (12) or a recycle stream (17) from the bottoms (10) from the absorption column. The purified carrier gas stream (18) leaves the apparatus at the top.

As a result of the above-described mode of operation, desublimation of DMT in the apparatus is prevented and the gas stream is cooled simultaneously without mist formation. A solid-free gas stream leaves the apparatus. During a process carried out in two separate apparatuses, integration of DMT removal and gas cooling in one absorption column makes more favorable operating and capital costs possible.

As a result of scrubbing of the gas with 1,4-butanediol, the material of value DMT is recirculated to the PBT process in a solvent intrinsic to the process and the total yield based on DMT is improved. The DMT can be recirculated directly without additional work-up steps to the esterification reactor in which DMT is catalytically esterified with 1,4-butanediol.

Compared to the previously known absorption processes using low-boiling solvents (e.g. methanol), the two-stage gas scrub using high-boiling 1,4-butanediol reduces the solvent loss via the gas leaving the scrubber. In addition, 1,4-butanediol has a high solvent capacity for DMT, so that no precipitation of solid from the liquid phase occurs. Circulation of the solvent is therefore possible. The space-time yield in the subsequent polycondensation process for preparing polyesters, in particular polybutylene terephthalate (PBT), PET or PTT, is therefore significantly increased.

EXAMPLE

DMT is stored at 170° C. in a storage tank. The gas atmosphere comprises 4.8% by weight of DMT and 95.2% by weight of nitrogen. During emptying of the tank, a gas stream of 41 kg/h typically leaves the tank. The gas stream is fed into a two-stage scrubber having a diameter of 200 mm and there was scrubbed in the lower section of the apparatus with 370 kg/h of pure 1,4-butanediol at 124° C. in countercurrent via separation-active internals. In the upper section of the apparatus, the gas is cooled by being conveyed in countercurrent to 125 kg/h of pure 1,4-butanediol at an inflow temperature of 60° C. over separation-active internals. The pure gas stream which has been cooled to 60.15° C. leaving the apparatus has a content of less than 0.1% by weight of butanediol and less than 0.2 ppm by weight of DMT. DMT balance: 99.98% DMT recovery In the example presented, gas and liquid passing from the lower section (hot BD as scrubbing medium) to the upper section (cold BD) of the apparatus have the following compositions:

| Phase | | Value |
|---|---|---|
| Gas | DMT | 24 ppm by weight |
| | 1,4-BD | 2.2% by weight |
| | N2 | 97.8% by weight |
| Liquid | DMT | 2.2 ppm by weight |
| | 1,4-BD | 99.99% by weight |
| | N2 | 14% by weight |

In the example presented, the gas phase leaving the apparatus has the following composition:

| Phase | | Value |
|---|---|---|
| Gas | DMT | 0.2 ppm by weight |
| | 1,4-BD | 0.07% by weight |
| | N2 | 99.93% by weight |

We claim:

1. A process for purifying and cooling a gas stream comprising a dialkyl ester A) of an aromatic dicarboxylic acid, which comprises treating the gas stream with an aliphatic dihydroxy compound B) at a temperature less than/equal to the melting point of the dialkyl ester A) in a 1$^{st}$ stage and treating the gas stream with an aliphatic dihydroxy compound B) in at least one second stage, wherein the dihydroxy compound B) has a temperature of less than/equal to 140° C. in the first stage and has a temperature of from 20 to 80° C. in the second stage, and wherein the temperature of the second stage is cooler than the temperature of the first stage.

2. The process according to claim 1, wherein the dialkyl ester A) is an ester of terephthalic acid, isophthalic acid, 2,6-naphthalenedicarboxylic acid or a mixture thereof.

3. The process according to claim 1, wherein the dialkyl ester A) has alkyl radicals having from 1 to 4 carbon atoms.

4. The process according to claim 1, wherein the gas stream which is purified and cooled is a laden inert gas stream.

5. The process according to claim 1, wherein the dihydroxy compound B) used is a diol having from 2 to 6 carbon atoms.

6. The process according to claim 1, wherein the dihydroxy compound B) used is 1,4-butanediol.

7. The process according to claim 1, wherein the dialkyl ester A) is dimethyl terephthalate.

8. The process according to claim 1, wherein the degree of saturation of the gas stream with respect to the dialkyl ester is less than/equal to 50%.

9. The process according to claim 1, wherein the gas stream contains less than 20 ppm by weight of the aromatic dialkyl ester A) after purification and cooling.

10. The process according to claim 1, wherein the temperature of the first stage is 140° C. to 50° C.

11. The process according to claim 1, wherein the temperature of the first stage is 136° C. to 60° C.

12. The process according to claim 1, wherein the temperature of the first stage is 124° C. to 110° C.

13. The process according to claim 1, wherein the temperature of the second stage is 50-70° C.

14. The process according to claim 1, wherein the temperature of the second stage is 50-70° C.

15. The process according to claim 10, wherein the temperature of the second stage is 50-70° C.

16. The process according to claim 11, wherein the temperature of the second stage is 50-70° C.

17. The process according to claim 12, wherein the temperature of the second stage is 50-70° C.

18. The process according to claim 10, wherein the temperature of the first stage is 140° C. to 50° C.

19. The process according to claim 11, wherein the temperature of the first stage is 136° C. to 60° C.

* * * * *